(12) United States Patent
Lohk

(10) Patent No.: US 9,179,826 B2
(45) Date of Patent: Nov. 10, 2015

(54) DISTAL TIP CHANNEL RAMP

(71) Applicant: Karl Storz GmbH & Co. KG, Tuttlingen (DE)

(72) Inventor: Margus Lohk, Harjumaa (EE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 4 days.

(21) Appl. No.: 13/651,137

(22) Filed: Oct. 12, 2012

(65) Prior Publication Data

US 2014/0107414 A1    Apr. 17, 2014

(51) Int. Cl.
*A61B 1/00* (2006.01)
*A61B 1/04* (2006.01)
*A61B 1/018* (2006.01)

(52) U.S. Cl.
CPC .............. *A61B 1/018* (2013.01); *A61B 1/0008* (2013.01); *A61B 1/0011* (2013.01)

(58) Field of Classification Search
CPC .............. A61B 1/0071; A61B 1/0098; A61B 1/00101; A61B 1/018
USPC ........... 600/104, 106, 107, 129, 127–13, 153, 600/154
See application file for complete search history.

(56) References Cited

U.S. PATENT DOCUMENTS

| | | | |
|---|---|---|---|
| 5,343,853 A * | 9/1994 | Komi | 600/107 |
| 5,976,077 A | 11/1999 | Wittens et al. | |
| 6,605,033 B1 * | 8/2003 | Matsuno | 600/107 |
| 7,341,555 B2 * | 3/2008 | Ootawara et al. | 600/106 |
| 2004/0249367 A1 * | 12/2004 | Saadat et al. | 600/101 |
| 2006/0264708 A1 * | 11/2006 | Horne | 600/130 |
| 2007/0249898 A1 * | 10/2007 | Otawara | 600/107 |
| 2008/0103410 A1 * | 5/2008 | Karpiel | 600/104 |
| 2008/0188862 A1 * | 8/2008 | Saitou | 606/113 |
| 2008/0215064 A1 * | 9/2008 | Motosugi | 606/113 |
| 2009/0287044 A1 | 11/2009 | Yamatani | |

FOREIGN PATENT DOCUMENTS

| | | |
|---|---|---|
| DE | 10348188 A1 | 5/2004 |
| EP | 1083821 B1 | 8/2009 |

* cited by examiner

*Primary Examiner* — Ryan Henderson
(74) *Attorney, Agent, or Firm* — Whitmyer IP Group LLC

(57) ABSTRACT

An endoscope and endoscope shaft having an adaptor that where the internal diameter of the adaptor increases along its longitudinal direction from the proximal end of the adaptor to the distal end of the adaptor. The adaptor guides an instrument through the working channel of the endoscope and prevents bumps from forming in the working channel of the endoscope shaft.

23 Claims, 4 Drawing Sheets

DISTAL TIP CHANNEL RAMP

FIELD OF THE INVENTION

The invention is directed to an endoscope shaft and endoscope having an adaptor in the distal tip of the endoscope shaft that guides an instrument through the working channel of the endoscope.

BACKGROUND OF THE INVENTION

Endoscopes having shafts that include working channels are known in the art. However, prior art endoscope shafts suffer from various deficiencies when passing an instrument, such as a forceps, through the working channel of an endoscope shaft. Such problems are exacerbated when the endoscope shaft is flexible and/or bendable.

Problems in prior art endoscopes include the working channel running over the edge of a push-pull wire bushing, which creates a bump in the working channel. A bump in the working channel may block instruments that are passed through the working channel. When this occurs, it is possible to feel an obstacle inside the working channel, which is disadvantageous. Furthermore, if instruments move over the bump several times, the instruments may wear a hole inside the wall of the working channel. This may cause the wall of the working channel to leak and may cause the endoscope to cease to be operational.

In prior art endoscopes, there are usually two or four wires in the endoscope and therefore there is typically more than one bushing within the endoscope, as the bushing typically includes at least one wire. Thus, there are multiple points where the working channel runs over a wire bushing and where the wire bushing presses against the channel. Thus, there are multiple points where a bump may be created in the working channel that can block instruments in prior art endoscopes.

Another disadvantage of the prior art includes having a complicated distal tip assembly procedure that is due to the limited space inside the endoscope shaft.

Thus, it is desirable to provide an endoscope and endoscope shaft assembly that solves the above mentioned problems in the prior art. The pending application is set to overcome these aforementioned disadvantages.

SUMMARY OF THE INVENTION

Accordingly, it is an object of the invention to provide an endoscope and endoscope shaft that overcomes the disadvantages of the prior art.

It is an object of the invention to allow the working channel to pass over a push-pull wire bushing without having a bump being created in the working channel, as the working channel runs over the push-pull bushing. It is another object of the invention for the working channel to guide instruments through the working channel without having instruments wear a hole inside the wall of the working channel.

These and other objects of the invention are achieved by providing an endoscope shaft having a proximal end and a distal end, the endoscope shaft comprising: a working channel extending from the proximal end of the endoscope shaft to the distal end of the endoscope shaft; and an adaptor located near the distal end of the endoscope shaft, the working channel being located within the adaptor, the adaptor guiding the working channel along its longitudinal direction from the proximal end of the adaptor to the distal end of the adaptor.

In certain embodiments, the adaptor has an internal diameter that increases along the longitudinal direction of the adaptor from the proximal end of the adaptor to the distal end of the adaptor.

In certain embodiments, the adaptor allows for instruments, when passing through the working channel, to have smooth access through the working channel. This is especially advantageous because insertion of the instruments is not hindered by a bump in the working channel. This is also especially advantageous when the endoscope shaft is flexible and/or bendable.

In certain embodiments, the internal diameter of the adaptor increases from a range between 0 degrees and 45 degrees relative to the longitudinal axis of the adaptor. In certain embodiments, the internal diameter of the adaptor increases at various degrees relative to the longitudinal axis of the adaptor along the length of the adaptor.

In certain embodiments, the adaptor is substantially cylindrical and includes a ramp built into the adaptor. In certain embodiments, the substantially cylindrical adaptor includes a top half and a bottom half, the ramp being built into the bottom half of the adaptor.

In certain embodiments, the height of the ramp from the bottom edge of the adaptor decreases from the proximal end of the adaptor to the distal end of the adaptor. In certain embodiments, the ramp has a radial edge surface that supports the working channel, the ramp being located within the lower half of the adaptor.

In certain embodiments, the ramp has two chamfered edges extending from the radial edge surface of the ramp. In certain embodiments, the ramp minimizes the sideways movement of the working channel. In certain embodiments, the ramp has a concave shape.

In certain embodiments, the distal end of the endoscope shaft includes a deflectable part that is made of multiple vertebrae, the multiple vertebrae extending from the distal end to the proximal end of the deflectable part. The deflectable part may be deflected via wires. The rest of the endoscope shaft is located proximal of the deflectable part. In certain embodiments, the rest of the endoscope shaft located proximal of the deflectable part may be a spiral made of metal or the like. This part may be flexible, but cannot be actively deflected.

In certain embodiments, the adaptor is located within the most distal vertebrae of the endoscope shaft.

In certain embodiments, the adaptor includes a connection surface at its distal and proximal ends, so that it rigidly fits within an endoscope shaft. In certain embodiments, the adaptor includes ribs at its distal and proximal ends. In certain embodiments, the adaptor includes various ridges so that it rigidly fits within an endoscope shaft.

In certain embodiments, the adaptor is made from various metals or various plastics. In certain embodiments, the adaptor is made from one or more metal and/or plastic materials.

In certain embodiments, the endoscope shaft further comprises a push-pull wire bushing, the push-pull wire bushing extending in the longitudinal direction, where the distal end of the push-pull wire bushing abuts the distal end of the adaptor or the ramp of the adaptor. In certain embodiments, the push-pull wire bushing extends in the longitudinal direction, and is abutting internal components within the endoscope shaft. In certain embodiments, the push-pull wire deflects the distal deflectable part of the shaft. In certain embodiments, the adaptor allows for the working channel to run over the edge of a push-pull wire bushing, while not creating a bump in the working channel as the edge of the working channel does not come into contact with the push-pull wire bushing. This prevents bumps from being created in the working channel.

In certain embodiments, the actuation of the push-pull wire bushing is controlled by a lever. In certain embodiments, the actuation of the push-pull wire bushing is controlled by an input button. In certain embodiments, the buttons are in combination with servo motors. In certain embodiments, the actuation of the push-pull wire bushing is controlled by a wheel or a joystick or can be controlled via a remote control.

In certain embodiments, the endoscope shaft further comprises an illumination source, the illumination source being located in the distal end of the endoscope shaft. In certain embodiments, the illumination source is an LED, infrared light, optical fiber or laser.

In certain embodiments, the working channel is flexible and/or bendable. In certain embodiments, the deflectable part of the distal end of the endoscope shaft is flexible and/or bendable.

In certain embodiments, the endoscope shaft further comprises an imager or fiber image bundle located within the endoscope shaft. In certain embodiments, a CMOS imager is located within the endoscope shaft. In certain embodiments, a circuit board and sensor are located within the endoscope shaft.

In certain embodiments, multiple vertebrae are located within the distal end of the endoscope shaft, allowing the distal end of the endoscope shaft to be bendable.

Other objects of the invention are achieved by providing an endoscope comprising: an endoscope shaft including: a working channel extending from the proximal end of the endoscope shaft to the distal end of the endoscope shaft, and an adaptor located near the distal end of the endoscope shaft, the working channel being located within the adaptor, the adaptor guiding the working channel along its longitudinal direction from the proximal end of the adaptor to the distal end of the adaptor; an imager; and an illumination source, the illumination source being located in the distal end of the endoscope shaft.

In certain embodiments, the adaptor has an internal diameter that increases along the longitudinal direction of the adaptor from the proximal end of the adaptor to the distal end of the adaptor.

In certain embodiments, the adaptor is substantially cylindrical and includes a ramp built into the adaptor. In certain embodiments, the substantially cylindrical adaptor includes a top half and a bottom half, the ramp being built into the bottom half of the adaptor. In certain embodiments, height of the ramp from the bottom edge of the adaptor decreases from the proximal end of the adaptor to the distal end of the adaptor.

In certain embodiments, the endoscope shaft is connected at its proximal end to a controller unit or to the body of the endoscope. In certain embodiments, the controller unit or body of the endoscope is connected to a display.

In certain embodiments, the controller unit includes at last one port, the least one port allowing for instruments to enter the working channel of the endoscope shaft. In certain embodiments, the controller includes a port allowing for insufflation gas to enter the working channel of the endoscope shaft. In certain embodiments, other ports are provides so that sensors and electronic components can be inserted into the endoscope shaft.

In certain embodiments, the controller includes a lever to control the flexibility and bending of the endoscope shaft. In certain embodiments, the controller includes various input devices to control the flexibility and bending of the endoscope shaft.

In certain embodiments, the controller includes various buttons to control various settings within the endoscope shaft. In certain embodiments, a camera is located within the controller or body of the endoscope. In other embodiments, a camera is located within the distal end of the endoscope shaft.

Other objects of the invention are achieved by providing an endoscope shaft having a proximal end and a distal end, the endoscope shaft comprising: a working channel extending from the proximal end of the endoscope shaft to the distal end of the endoscope shaft; and a sleeve located at the distal end of the endoscope shaft, the working channel being located within the sleeve, the sleeve including an adaptor, the adaptor having a diameter that increases along the longitudinal direction of the adaptor from the proximal end of the adaptor to the distal end of the adaptor.

In certain embodiments, the adaptor is integrated within the sleeve.

In certain embodiments, the endoscope shaft further includes an optics module with a CMOS image sensor (positioned vertically in the shaft).

In certain embodiments, a flexible circuit board is connected to the image sensor and runs all the way to the proximal end of the shaft. The push-pull wire connects the vertebrae with the proximal end of the endoscope and allows for deflection of the distal end of the shaft with a lever.

In certain embodiments, the endoscope is a video endoscope.

In certain embodiments, the adaptor with integrated ramp is located between the distal tip and deflectable or active section of the endoscope shaft. In certain embodiments, the adaptor and the ramp are directly integrated into the last distal vertebrae. Both of these embodiments give the flexible working channel a firm up direction over the push-pull wire bushings at the center of the vertebrae assembly. This prevents bumps from forming in the working channel.

In certain embodiments, the radial shape of the ramp minimizes the flexible working channel moving sideways when the instrument active section is bending up and down (or left and right).

In certain embodiments, the working channel is guided in the middle of the vertebrae and endoscope shaft so that bumps are not created in the working channel.

In certain embodiments, the adaptor has an internal diameter that increases from the proximal to the distal end of the adaptor. In certain embodiments, the external diameter of the adaptor remains constant from the proximal to the distal end of the adaptor. In certain embodiments, the external diameter of the adaptor decreases from the proximal to the distal end of the adaptor.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 1:
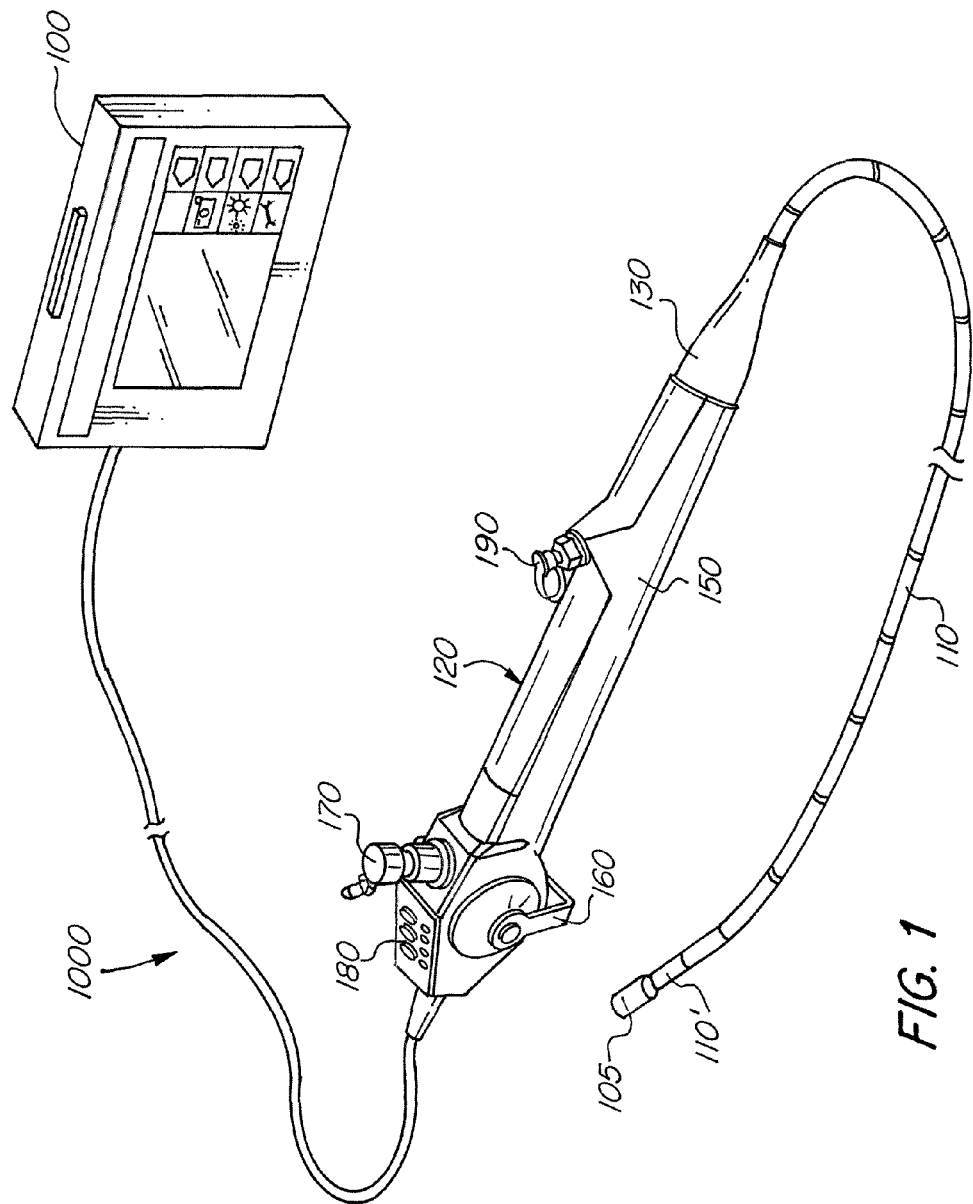
FIG. 1 is a perspective view of an endoscope of an embodiment of the invention.

Referring to FIG. 1, a perspective view of an endoscope system 1000 is shown. FIG. 1 shows an endoscope 120 having a connector component 130 connecting the controller or body 150 of the endoscope 120 to the endoscope shaft 110. The endoscope shaft 110 is shown as having marks along the length of the endoscope shaft, so that a user can tell how far the endoscope shaft has been inserted into the body.

The endoscope of FIG. 1 shows port 170 and port 190. Port 190 allows for instruments to be inserted to the endoscope shaft 110. Port 170 allows for insufflation elements to allow gas to be inserted into the endoscope shaft 110.

In FIG. 1, lever 160 is also shown connected to the body 150 of the endoscope. Lever 160 allows for articulation of the endoscope. The endoscope is also shown being attached via a cable to a display 100. The display 100 shows images from the imager in the distal tip 105 of the endoscope 120 when in use.

Figure 2:
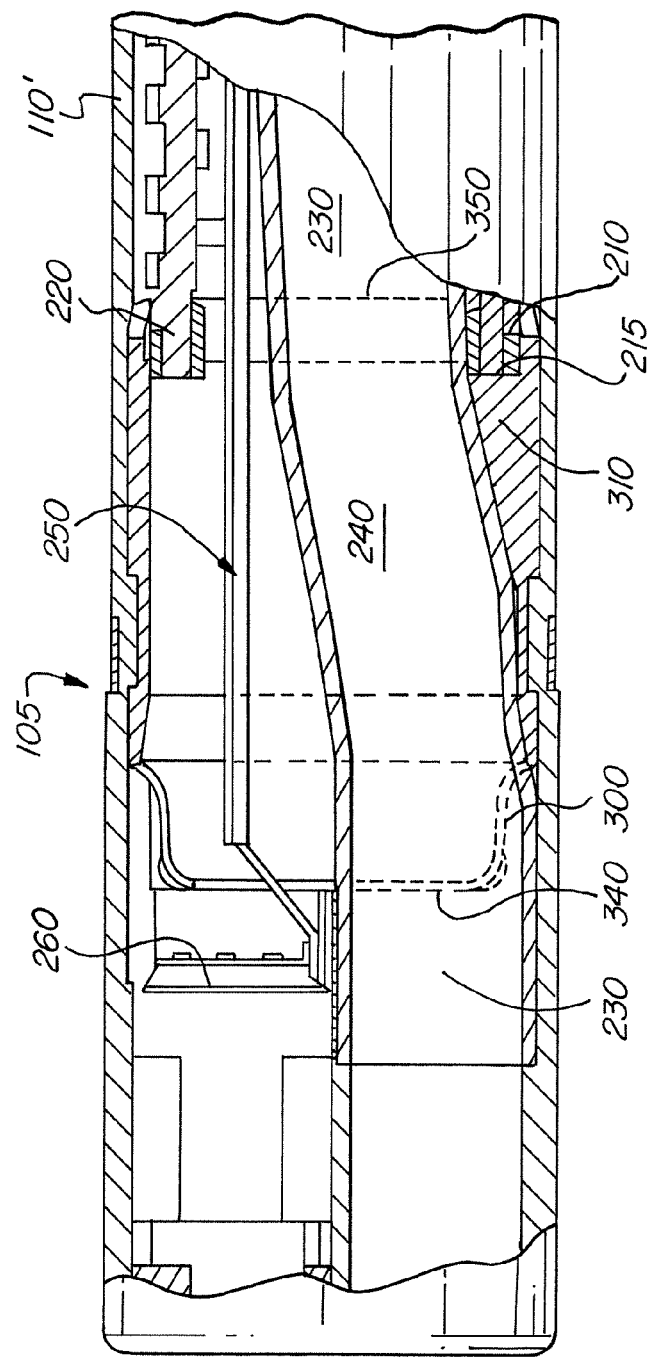
FIG. 2 is a detailed longitudinal cross section view of the distal tip of the endoscope shaft of FIG. 1.

FIG. 2 shows a longitudinal cross section of the distal tip 105 of the endoscope. Here, working channel 230 is shown with the adaptor 300 housing a portion 240 of the working channel 230. Also shown is optics module 260 with CMOS image sensor (positioned vertically in the shaft). Flexible circuit board 250 is shown connected to the image sensor. Flexible circuit board 250 runs all the way to the proximal end of the endoscope shaft. Also shown is push-pull wire 210, which is used to deflect the distal deflectable part of the shaft the endoscope shaft 105/110'.

Focusing more in detail, adaptor 300 is shown in partial broken line form. The adaptor 300 is shown housing part of the working channel 230 of the endoscope shaft. The distal end 340 of the adaptor is shown as well as the proximal end 350.

The adaptor 300 includes ramp 310, which supports the portion 240 of working channel 230 that is within the adaptor 300. The ramp is shown as having its height decrease from the proximal end 350 to the distal end 340.

When an instrument is inserted into the working channel 230, the ramp 310 allows it to pass over the problematic area of the push-pull wire bushing 210, which, in prior art systems, causes a bump to form in the working channel. As shown, the ramp prevents this bump from occurring.

FIG. 2 also shows multiple vertebrae 220, which allow the distal end of the endoscope shaft 105/110' to be flexible and/or bendable during actuation. The deflectable part of the endoscope shaft is shown as 105/110'.

Figure 3:
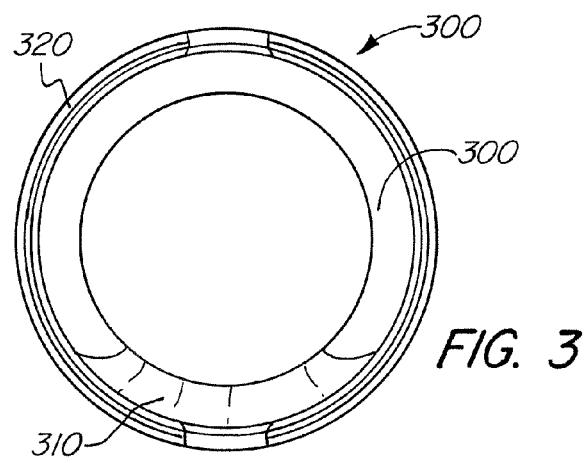
FIG. 3 is a front view of an adaptor of an embodiment of the invention.

FIGS. 3-6 show various views of adaptor 300. FIG. 3 is a front view of the adaptor showing inside surface 330 of the adaptor, ramp 310 and outer surface 320.

Figure 4:
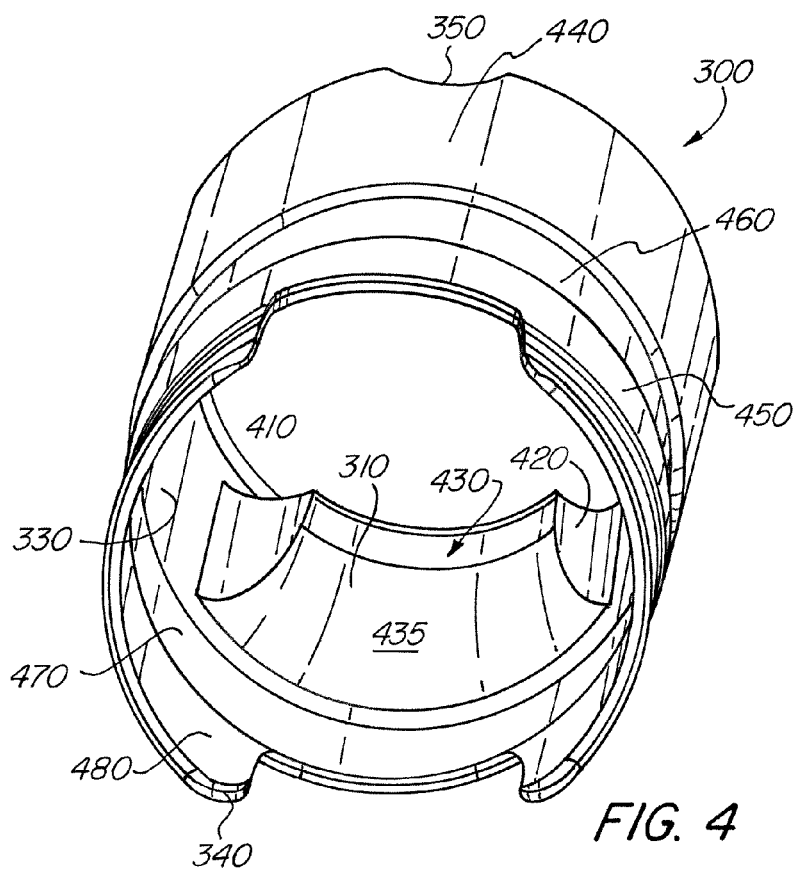
FIG. 4 is a perspective view of the adaptor of FIG. 3.

FIG. 4 is a perspective view of the adaptor 300 showing the ramp 310. The ramp 310 has a radial surface 430/435 that supports the working channel 230. The radial surface 430/435 prevents the working channel 230 from moving sideways or up and down when the distal deflectable part of the endoscope shaft is actuated. The ramp 310 also includes chamfered edges 410 and 420. The inner surface 330 of the adaptor 300 houses the ramp 310.

Also shown are outer surface parts 440, 450 and 460 which make up the outer surface 320 of the adaptor 300. The inner surface of the distal tip 480 is also shown. The inner surface 480 of the distal tip may have ribs or may have a connection element so that the adaptor can be fixed within the distal tip 105 of the endoscope shaft 110. In certain embodiments, the adaptor 300 can be fixed partially within the distal tip 105 and endoscope shaft 110', where endoscope shaft 110' represents the last active section or deflectable section of the endoscope shaft 110.

Figure 5:
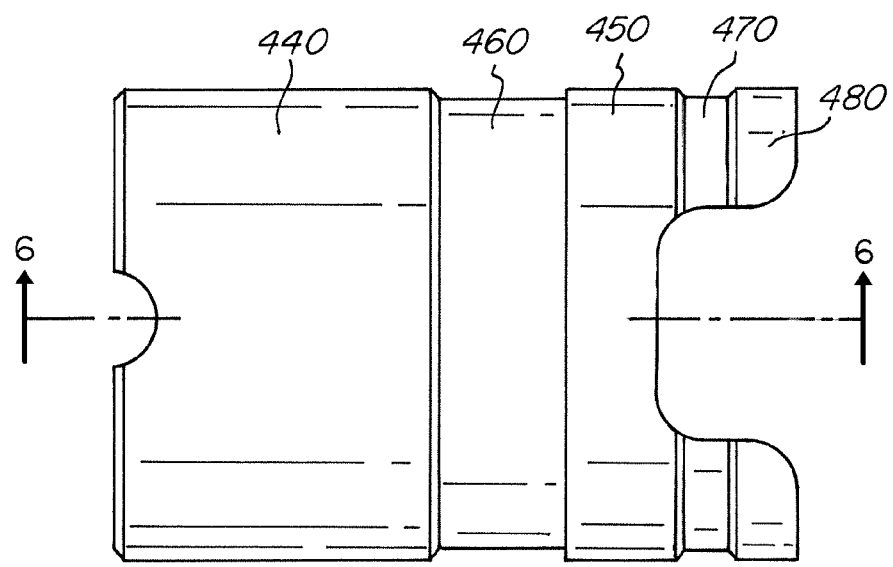
FIG. 5 is a side view of the adaptor of FIG. 3.
Figure 6:
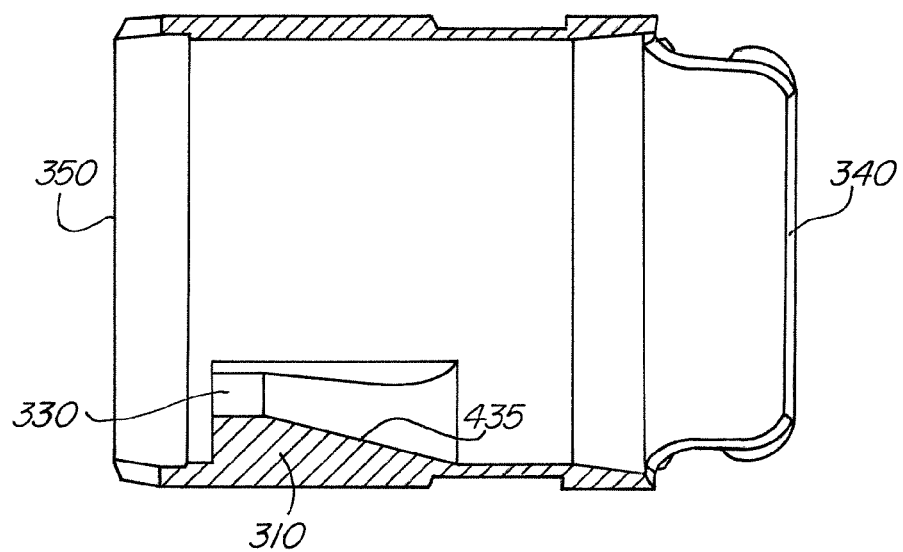
FIG. 6 is a longitudinal cross section view of the adaptor of FIG. 3.

FIGS. 5-6 show a side view and longitudinal cross section view of the adaptor 300. FIG. 5 shows that the adaptor has multiple exterior portions 440, 460, 450, 470 and concluding with the distal end 480 of the adaptor 300.

FIG. 6 shows the cross section of the adaptor where the internal diameter of the adaptor increases from the proximal end 350 of the adaptor to the distal end 340 of the adaptor 300. As shown, the adaptor has a connecting region prior to the region where the internal diameter of the adaptor begins to increase. This connecting region allows the adaptor 300 to be fixed within the distal tip of the endoscope.

Ramp radial surface area 435 and ramp 310 are shown in FIG. 6. Also shown is the curvature of the adaptor 300, where the adaptor can have multiple cut out portions at its proximal 350 and distal 340 ends, so that it can be fixed within the distal tip 105 of an endoscope shaft 110.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. An endoscope shaft having a proximal end and a distal end, the endoscope shaft comprising:
    a working channel, the working channel extending from a proximal end of the endoscope shaft to the distal end of the endoscope shaft, the working channel extending through the distal end of the endoscope shaft so that an instrument is able to pass through the distal end of the endoscope shaft and exit the distal end of the endoscope shaft parallel or essentially parallel to a longitudinal axis of the endoscope shaft;
    an adaptor located near the distal end of the endoscope shaft, the working channel being located within the adaptor, the adaptor guiding the working channel along the longitudinal direction of the adaptor from a proximal end of the adaptor to a distal end of the adaptor, the adaptor having an internal cross-sectional area that increases from a proximal end of a ramp built into the adaptor to a distal end of the ramp, the ramp being formed as a single piece structure with the adaptor;
    a push-pull wire bushing, the push-pull wire bushing extending in a longitudinal direction, where a distal end of the push-pull wire bushing abuts the proximal end of the adaptor, the ramp built into the adaptor allowing the instrument to pass over the push-pull wire bushing; and a push-pull wire disposed within the push-pull wire bushing, wherein the push-pull wire can reciprocate longitudinally to deflect the distal end of the endoscope shaft, wherein the adaptor is fully enclosed within the endoscope shaft and the distal end of the adaptor terminates proximal a distal end of the working channel, wherein the working channel comprises a flexible tube disposed within the endoscope shaft.

2. The endoscope shaft of claim 1, wherein the adaptor is substantially cylindrical.

3. The endoscope shaft of claim 2, wherein the substantially cylindrical adaptor includes a top half and a bottom half, the ramp being built into the bottom half of the adaptor.

4. The endoscope shaft of claim 2, wherein a height of the ramp from a bottom edge of the adaptor decreases from the proximal end of the ramp to the distal end of the ramp.

5. The endoscope shaft of claim 2, wherein the ramp has a radial edge surface that supports the working channel, the ramp being centrally located within the adaptor.

6. The endoscope shaft of claim 5, wherein the ramp has two chamfered edges extending from the radial edge surface of the ramp.

7. The endoscope shaft of claim 2, wherein the ramp minimizes sideways movement of the working channel.

8. The endoscope shaft of claim 1, wherein the distal end of the endoscope shaft includes a deflectable part made of multiple vertebrae, the multiple vertebrae extending from a distal end to a proximal end of the deflectable part.

9. The endoscope shaft of claim 8, wherein the adaptor is located within a most distal vertebrae of the endoscope shaft.

10. The endoscope shaft of claim 1, wherein the working channel is flexible.

11. The endoscope shaft of claim 1, further comprising an illumination source, the illumination source being located in the distal end of the endoscope shaft.

12. The endoscope shaft of claim 1, further comprising an imager or fiber image bundle located within the endoscope shaft.

13. The endoscope shaft of claim 1, wherein the distal end of the endoscope shaft having an opening along its longitudinal direction.

14. The endoscope shaft of claim 1, wherein the adaptor is oriented parallel to the longitudinal axis of the endoscope shaft.

15. The endoscope shaft of claim 1, wherein the distal end of the adaptor is located proximally to the distal end of the endoscope shaft.

16. The endoscope of claim 1, wherein the ramp is formed within the adaptor to create a smooth access through the working channel.

17. An endoscope comprising:
an endoscope shaft including:
a working channel extending from a proximal end of the endoscope shaft to a distal end of the endoscope shaft, the working channel extending through the distal end of the endoscope shaft so that an instrument is able to pass through the distal end of the endoscope shaft and exit the distal end of the endoscope shaft parallel or essentially parallel to a longitudinal axis of the endoscope shaft,
an adaptor located near the distal end of the endoscope shaft, the working channel being located within the adaptor, the adaptor guiding the working channel along the longitudinal direction of the adaptor from a proximal end of the adaptor to a distal end of the adaptor, the adaptor having an internal cross-sectional area that increases from a proximal end of a ramp built into the adaptor to a distal end of the ramp, the ramp formed as a single piece structure with the adaptor, and
a push-pull wire bushing, the push-pull wire bushing extending in a longitudinal direction, where a distal end of the push-pull wire bushing abuts the proximal end of the adaptor, the ramp built into the adaptor allowing the instrument to pass over the push-pull wire bushing;
a push-pull wire disposed within the push-pull wire bushing, wherein the push-pull wire can reciprocate longitudinay to deflect the distal end of the endoscope shaft,
wherein the adaptor is fully enclosed within the endoscope shaft and the distal end of the adaptor terminates proximal a distal end of the working channel,
wherein the working channel comprises a flexible tube disposed within the endoscope shaft;
an imager; and
an illumination source, the illumination source being located in the distal end of the endoscope shaft.

18. The endoscope of claim 17, wherein the adaptor is substantially cylindrical and includes a ramp bunt into the adaptor.

19. The endoscope of claim 18, wherein the substantially cylindrical adaptor includes a top half and a bottom half, the ramp being built into the bottom half of the adaptor.

20. The endoscope of claim 18, wherein a height of the ramp from a bottom edge of the adaptor decreases from the proximal end of the ramp to the distal end of the ramp.

21. The endoscope of claim 17, wherein the distal end of the endoscope shaft includes a deflectable part made of multiple vertebrae, the multiple vertebrae extending from a distal end to a proximal end of the deflectable part.

22. An endoscope shaft having a proximal end and a distal end, the endoscope shaft comprising:
a working channel extending from a proximal end of the endoscope shaft to the distal end of the endoscope shaft;
a sleeve located near the distal end of the endoscope shaft, the working channel being located within the sleeve, the sleeve including an adaptor, the adaptor guiding the working channel along a longitudinal direction of the adaptor from a proximal end of the adaptor to a distal end of the adaptor, the adaptor having an internal cross-sectional area that increases from a proximal end of a ramp built into the adaptor to a distal end of the ramp, the ramp formed as a single piece structure with the adaptor, such that a medical instrument exits the distal end of the endoscope shaft parallel or essentially parallel to a longitudinal axis of the endoscope shaft;
a push-pull wire bushing, the push-pull wire bushing extending in a longitudinal direction, where a distal end of the push-pull wire bushing abuts a proximal end of the adaptor, the ramp built into the adaptor allowing the instrument to pass over the push-pull wire bushing; and
a push-pull wire disposed within the push-pull wire bushing, wherein the push-pull wire can reciprocate longitudinally to deflect the distal end of the endoscope shaft,
wherein the adaptor is fully enclosed within the endoscope shaft and the distal end of the adaptor terminates proximal a distal end of the working channel,
wherein the working channel comprises a flexible tube disposed within the endoscope shaft.

23. The endoscope of claim 22, wherein the adaptor is substantially cylindrical.

* * * * *